United States Patent [19]

Ham

[11] 4,159,893
[45] Jul. 3, 1979

[54] METHOD OF TESTING A LANDFILL FOR ITS METHANE POTENTIAL

[75] Inventor: Robert K. Ham, Madison, Wis.

[73] Assignee: Reserve Synthetic Fuels, Inc., Signal Hill, Calif.

[21] Appl. No.: 857,574

[22] Filed: Dec. 5, 1977

[51] Int. Cl.² .............................................. G01N 33/24
[52] U.S. Cl. ................................................ 23/230 EP
[58] Field of Search .................................... 23/230 EP

[56] References Cited

U.S. PATENT DOCUMENTS

| 3,120,428 | 2/1964 | McDermott | 23/230 EP |
| 3,847,549 | 11/1974 | Schorno | 23/230 EP |
| 4,000,990 | 1/1977 | Bingham | 55/30 |
| 4,067,693 | 1/1978 | Wimberley | 23/230 EP |

FOREIGN PATENT DOCUMENTS 443965  6/1975  U.S.S.R. ................................ 23/230 EP

OTHER PUBLICATIONS

*Energy Recovery Sanitary Landfills—A Review*, W. C. Boyle, Microbial Energy Conversion, proceedings of seminar held in Gottingen, West Germany, 10/4-8/76, pp. 119, 124-126.

*Comprehensive Studies of Solid Waste Management*, C. G. Golveke, USEPA report SW-10rg, 3rd annual report, Univ. of California (1971), pp. 82-87; 110; 113-133.

LeNormand et al., "Degradation of Ground Waste Material in Garbage," Chemical Abstract, vol. 84, 1976, No. 84:79273g.

*Primary Examiner*—Arnold Turk
*Attorney, Agent, or Firm*—Gordon L. Peterson

[57] ABSTRACT

Method of testing a landfill for its methane potential comprising selecting a landfill which contains a significant decomposable fraction and a significant non-decomposable fraction, locating a plurality of zones within the landfill with each of said zones having at least one different characteristic, taking at least one sample of the material of the landfill at each of the zones, measuring the content of each of the fractions of each of the samples, and utilizing the ratio of one of the fraction contents to the other of the fraction contents for at least some of the samples to find the approximate methane potential of the landfill.

11 Claims, 4 Drawing Figures

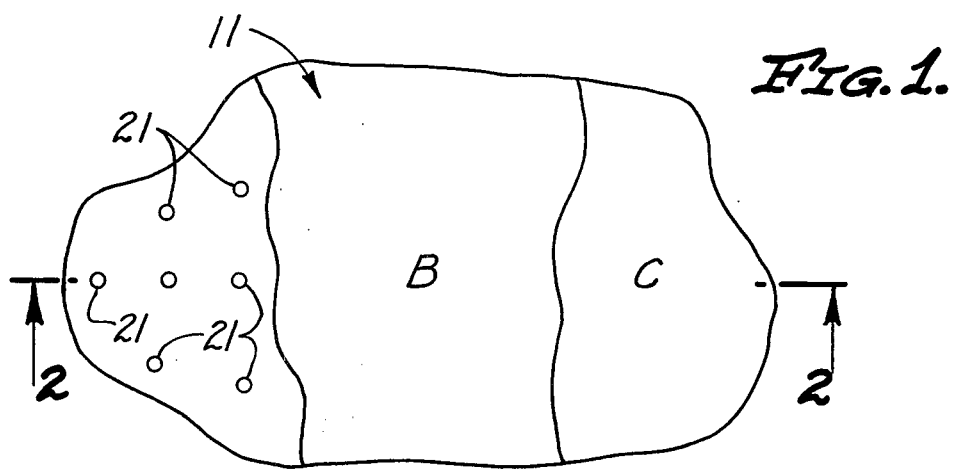
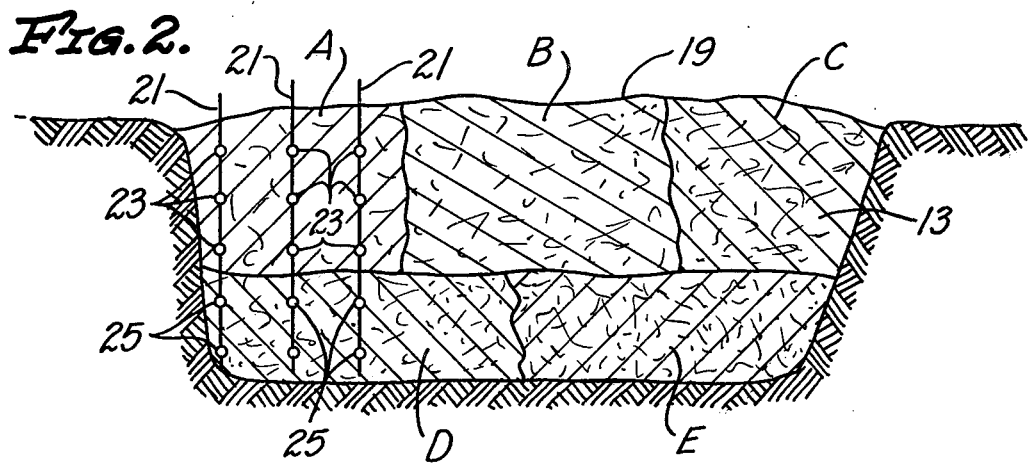
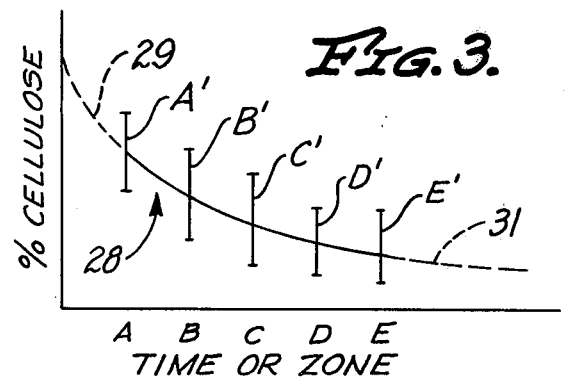
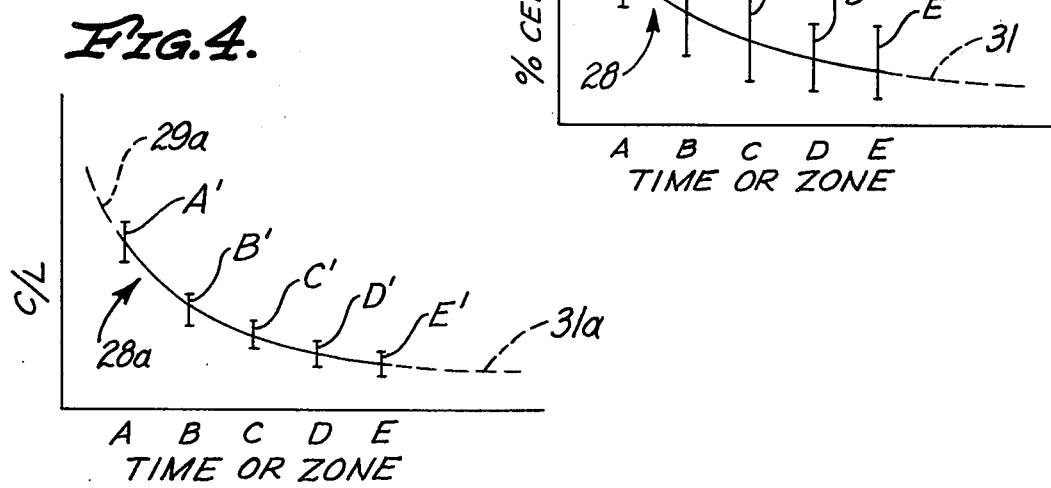

METHOD OF TESTING A LANDFILL FOR ITS METHANE POTENTIAL

BACKGROUND OF THE INVENTION

Decomposition of materials within a landfill produces landfill gas which contains methane. In some instances, the methane concentration is sufficient to warrant recovery of the landfill gas so that the methane can be used as a fuel. To increase the concentration of methane, a methane purification plant can be installed at the landfill.

The recovery of landfill gas and its purification requires a substantial investment for the construction of the necessary recovery and purification plant. Before making an investment of this magnitude, it is necessary to determine the methane potential of the landfill. The fact that a landfill is generating methane in economically recoverable quantities today is no guarantee that the landfill will continue to generate economically recoverable quantities of methane for a sufficient period to amortize the cost of the plant and to continue to defray the operating costs of the plant.

Unfortunately, very little is known about methane production in landfills and only theoretical, idealized approaches to establishing methane potential have been used. In one prior art process, a sample is taken from incoming refuse to a landfill and chemically analyzed. A stoichiometric equation is then used to approximate the methane yield. This approach does not provide any information as to the amount of methane already generated by the landfill nor does it show the rate at which the methane will be produced by the landfill over a period of time. Furthermore, this approach does not adequately take into account the changes in methane production and methane production rates found in various portions of the landfill.

Experimental laboratory studies have also been used in an effort to determine methane potential. Typically, in an experimental laboratory study, an effort is made to simulate a landfill. The flow rate of gas from the simulated fill is measured and the gas is chemically analyzed. From this, methane potential is estimated. Unfortunately, it has not been possible to accurately simulate actual landfill conditions. Moreover, the experimental studies are ordinarily conducted, out of necessity, over a relatively short period of time, such as six to eight months, whereas actual landfill gas production may occur over a ten to twenty-year period. There are indications that the balance between the microrganisms may be significantly different on these short-time tests than in a real landfill.

The problem of determining the methane potential is complicated because landfills are generally not homogeneous. For example, the composition of material within a landfill and the time of placement of the refuse in the landfill will vary. In addition, moisture content, permeability of the refuse, and air contamination of the landfill can affect methane generation, and these characteristics may vary from one location to another within the same landfill.

SUMMARY OF THE INVENTION

Cellulose is a major decomposable substance found in most landfills. Cellulose is the major chemically identifiable component of refuse which decomposes in a landfill to produce methane. Landfills typically contain other ingredients which decompose to produce methane. However, the methane produced from these other ingredients is typically small when compared with the methane derived from the cellulose. Accordingly, determining the methane obtainable from just the cellulose typically provides a conservative estimate of the methane potential of the landfill. This invention, among other things, provides a process for finding the approximate methane potential of the landfill by ascertaining the approximate portion of the landfill which is made up of a selected fraction where the selected fraction includes cellulose as a major component.

To obtain the most accurate results, the selected fraction preferably consists essentially of cellulose. However, if desired, the selected fraction may contain other components. The minimum allowable percentage of cellulose in the selected fraction cannot be determined with mathematical precision, but generally the accuracy of the methane potential predictions can be expected to degrade as the amount of cellulose in the selected fraction is reduced. If the selected fraction is not essentially cellulose, it may be, or include for example, volatile solids or carbohydrates.

For the purposes of the primary discussion hereinbelow, it is assumed that the selected fraction consists essentially of cellulose. However, from the foregoing, it should be understood that the selected fraction need not consist essentially of cellulose.

Cellulose measurements have been used to indicate the extent of decomposition in aerobically decomposed organic material, such as compost. However, this is a rather short-term aerobic decomposition process which may last, for example, for six months, whereas sanitary landfill decomposition for methane production occurs anaerobically over a span of many years, such as twenty years. With respect to anaerobic decomposition of non-landfill materials, such as sanitary sludges, volatile solids and related parameters have been used as a measure of the state of decomposition. However, materials of this type typically decompose over a time span which is very short compared with the decomposition process in a sanitary landfill.

Unfortunately, ascertaining the amount of cellulose in a landfill is not easy, and this is due in substantial part to the nonhomogeneous nature of landfills. With this invention, the landfill is divided into zones with each significant portion of the landfill, which acts substantially uniformly with respect to cellulose decomposition, forming one zone. Only portions of the landfill which are significant in terms of methane production are dealt with because it would be totally impractical to consider smaller quantities of the landfill.

The composition of refuse within a landfill varies widely and may include, for example, paper, wood, metal, plastics, etc. Each zone will, of course, have a variety of different kinds of material in it. Obviously, therefore, each zone will have individually small components that act differently with respect to cellulose decomposition. However, notwithstanding these factors, it is reasonably possible to divide the landfill into relatively large zones based upon different characteristics so that each of the zones may be considered as acting substantially uniformly with respect to cellulose decomposition.

Various characteristics can be used to distinguish one zone from another. A preferred characteristic is the time of placement of the refuse in the landfill. Because cellulose decomposes over a period of time, refuse placed at an early date in the landfill would be expected to have less cellulose than refuse placed recently. If the landfill is otherwise relatively free of factors which may cause cellulose in portions of the landfill to decompose at a rate inconsistent with its length of time of placement in the landfill, it may be necessary to select zones only on the basis of time of placement.

However, the landfill may have other characteristics that require that it be divided into additional zones. For example, if a portion of the landfill is submerged in water, the submerged portion should be considered separately from the non-submerged portion. Similarly, the upper layer of the landfill may be considered as a separate zone if it is believed that the upper layer may have responded differently due to weather variations or if it is believed that air may have infiltrated into the upper layer to poison the methane-producing process.

Several divisions and subdivisions may be used if necessary to establish all of the zones within the landfill. For example, if part of the landfill is submerged, then the submerged portion may itself be divided into zones based upon time of placement and the nonsubmerged portion divided into additional zones also based upon time of placement.

After the zones have been located, at least one sample is taken from the material of the landfill in each of the zones. Preferably, samples are taken from a multiplicity of locations within each zone, and a plurality of samples should be taken from each such location. For example, three to five samples may be taken from each location and samples which appear spurious discarded. The sampling locations within each zone may be at different depths and different positions horizontally within the zone. The overall purpose of the sampling technique is to obtain a representative sample of the refuse within that zone.

After the samples are taken, the cellulose content, or the selected fraction content as the case may be, of each of the samples is measured and any spurious samples are discarded. The percent by weight of each zone which is made up of cellulose as of the sampling date can be calculated. This can be multiplied by the weight of refuse within each zone to find the amount of cellulose remaining in that zone. The weight of refuse within each zone can be estimated in a variety of different ways, including the use of landfill records and by approximating the volume of each zone and using approximate landfill density figures. With this information, the amount of methane potential arising from cellulose decomposition for each zone and for the entire landfill can be determined.

By utilizing the cellulose content for each of the zones, a curve can be plotted which shows the rate of cellulose decomposition within the landfill. Accordingly, the methane potential can be determined for any time period. Thus, "methane potential" as used herein means the methane producing ability of the landfill for any period of time following the sample date. "Methane potential" as used herein is not limited to the theoretical maximum methane production of the landfill over an infinite time span beginning with the sampling date. Rather, the term "methane potential" also means the methane-producing capacity of the landfill over any time span which is less than the time required for the landfill to fully convert all of the methane-producing materials therein to methane.

Of course, the cellulose may be converted into another substance, such as sugar, during analytical procedures following sampling. In this event, all of the steps subsequent to the conversion are carried out on such substance. In order to cover such conversions that may take place during analytical procedures, the term "cellulose" as used herein means cellulose and any substance into which the cellulose is converted during analytical procedures following sampling.

Because of the nonhomogeneous character of landfills, the cellulose content of samples taken from the same zone may vary significantly. Accordingly, to reduce sampling errors, it is very desirable to measure the content of a suitable significant nondecomposable fraction in each of the samples. The nondecomposable fraction should be one, the quantity of which varies with the quantity of cellulose in the refuse at the time of placement. For example, the preferred nondecomposable fraction is, or includes, lignin. In originally placed refuse, the quantity of lignin can reasonably be expected to vary with the quantity of cellulose. Accordingly, a sample which shows, by way of example, a relatively high cellulose content, would also show a relatively high lignin content, and conversely, a sample showing a relatively low cellulose content would be expected to show a relatively low lignin content. The cellulose-to-lignin ratios for each of these two samples would not ordinarily vary nearly as much as the cellulose content alone. Thus, the ratio significantly reduces sampling errors caused by the local nonhomogeneous nature of landfills and permits the plotting of a more accurate curve showing cellulose decomposition rates. Use of this ratio also permits landfill tonnage records to be used in calculating the weight of cellulose available for decomposition in the selected time span.

In a broader sense, the ratio need not be cellulose to lignin but may be a significant first fraction to a significant nondecomposable fraction where the first fraction includes decomposable material. In this instance, the decomposable material may be any material, the decomposition of which is related to methane production, and both fractions should be of the type, the content of which varies together in refuse at the time of placement in the landfill. For example, inorganic materials, such as total ash content, may be used in lieu of lignin.

The invention, together with further features and advantages thereof may best be understood by reference to the following description taken in connection with the accompanying illustrative drawings.

BRIEF DESCRIPTION OF THE DRAWING

FIG. 1 is a plan view of a landfill on which the process of this invention can be carried out.

FIG. 2 is a sectional view taken generally along line 2—2 of FIG. 1 with the vertical dimension of the landfill exaggerated.

FIG. 3 is a plot of cellulose in the landfill versus time.

FIG. 4 is a plot of the cellulose-to-lignin ratio versus time.

DESCRIPTION OF THE PREFERRED EMBODIMENT

FIGS. 1 and 2 show a sanitary landfill 11 of the type on which the process of this invention is adapted to be carried out. The landfill 11 is of the type in which anaerobic decomposition produces a landfill gas which includes methane. Although the landfill 11 can be formed in different ways, in the form shown in FIGS. 1 and 2, it is formed by depositing refuse 13 in a cavity or excavation 15 in the earth 17. Descriptions of the various types of landfill design are well covered in the solid waste disposal literature. The landfill 11 has an upper surface 19 which is exposed at the top of the landfill. Although the landfill 11 is of the type which is deposited in an excavation, the process of this invention is equally applicable to other kinds of landfills, such as the landfills described in the literature referred to above.

After determining that the landfill 11 should be tested for its methane potential, zones A,B,C,D, and E of the landfill are identified and located. Each significant portion of the landfill 11 which acts substantially uniformly with respect to cellulose decomposition is identified as one of the zones A-E. The number of zones selected and identified for a given landfill will vary in accordance with the characteristics of the landfill. In addition, more accurate results should be obtainable with the process as the number of zones selected for a given landfill increases. On the other hand, the time and expense in carrying out the process of this invention will also increase as the number of zones selected increases.

Each of the zones A-E is distinguishable from the other zones by at least one characteristic. Although different characteristics may be utilized in the landfill 11, the characteristic which distinguishes each of the zones A-E is time of placement in the landfill. The zones A-E were placed in the landfill in the order of zone E to zone A with zone E being placed first.

The amount of time to identify each of the zones A-E should be selected so that a plurality of zones is established for each landfill to be tested. For example, in a twenty-year-old landfill, each zone may represent several years, and in a five-year-old landfill, each zone may represent only six months of refuse placement. Although any number of zones can be established, it will ordinarily be desirable to have at least about five to ten zones based upon time of placement in the landfill.

Although the selection of the zones A-E in the landfill 11 is based upon time of placement, it should be noted that the bottom portion of the landfill is in one set of zones and the upper portion of the landfill containing the upper surface 19 of the landfill is in other zones. Thus, in this example, a separation of the zones A-E based upon time of placement in the landfill also inherently separates the upper and lower regions of the landfill so that they are part of separate zones. Accordingly, the upper zones A-C which may be more subject to weather changes are separated from the lower zones D and E which are less subject to weather variations.

After the zones A-E are selected, a plurality of samples is taken from each of the zones. The primary purpose of the sampling procedure is to obtain a representative sample of each of the zones. Any sampling technique which is reasonably calculated to obtain this objective can be used.

For example, each of the zones is preferably sampled at several different horizontally spaced locations and at several different vertically spaced locations. By way of illustration, the zone A is sampled along seven horizontally spaced sampling axes 21. The sampling axes 21 are arranged so that some of them lie adjacent the periphery of the zone A, as well as the periphery of the landfill 11, while others extend through interior portions of the zone A. A plurality of vertically spaced sampling locations 23 lie along each of the sampling axes 21. In the form shown in FIGS. 1 and 2, three sampling locations 23 lie along each of the sampling axes 21 within the zone A and two vertically spaced sampling locations 25 lie along each of the sampling axes 21 in the zone E. Of course, samples may be taken at greater number or a lesser number of depths than shown by way of example in FIG. 2. Sampling locations 23 along each of the sampling axes 21 are located so that samples are taken at the upper, lower and central regions of the zone A. Preferably, three to five samples are taken at each of the sampling locations 23.

The samples may be taken using any suitable sampling technique. For example, samples may be taken as refuse is brought to the surface of the landfill 11 during drilling. In other instances, digging devices, such as front-end loaders or backhoes may be used. The size of each sample is determined by the handling procedures and analytical requirements, and it has been found that samples in the one kilogram range are satisfactory.

The cellulose and lignin content of each of the samples is then measured. This can be accomplished utilizing standard analytical procedures. For example, each of the samples is first dried, to remove substantially all of the water, and weighed, both before and after drying to determine the moisture content. The dry samples are then finely shredded. The shredded samples are analyzed, both quantitatively and qualitatively, for percent by weight of celulose, lignin, combustible or organic matter. The following table shows by way of example an analysis of several samples taken from refuse approximately one year old:

| Sample No. | % $H_2O$ | % Cellulose | % Volatile | % Lignin |
|---|---|---|---|---|
| 1 | 56.0 | 19.7 | 49.1 | 14.0 |
| 2 | 53.3 | 23.1 | 50.1 | 12.6 |
| 3 | 55.1 | 29.1 | 58.9 | 18.3 |
| 4 | 54.7 | 22.4 | 47.8 | 13.6 |
| 5 | 53.4 | 30.4 | 56.8 | 15.9 |
| 6 | 52.6 | 25.1 | 49.5 | 13.9 |
| 7 | 49.6 | 33.6 | 57.8 | 13.9 |
| 8 | 50.8 | 37.5 | 64.5 | 8.7 |
| 9 | 48.8 | 37.7 | 66.4 | 14.5 |

In the above table, the percents are by weight and all of the percentages, except for water, are on a dry basis.

In ascertaining the methane potential of the landfill, it is useful to express the percent cellulose of each of the samples as a percent of the dry weight of each such sample. This is of interest because cellulose is the largest specifically identifiable component which decomposes in a landfill to provide a source of methane production. FIG. 3 is a plot of the percent cellulose as a percent of dry weight of the samples against time of placement of the refuse in the landfill. The percent cellulose figures for each of the samples for zone A will typically vary, and this variation is represented graphically by a vertical bar A′ which represents the total variation in cellulose content for the samples taken from zone A. Similarly, the percent cellulose data for the zone B-E is correspondingly plotted to define bars B′-E′, respectively.

A curve 28 (FIG. 3) is then drawn through the bars A′-E′ using known statistical procedures so that it represents the approximate cellulose content of each of the zones A-E. The curve 28 of FIG. 3 is useful because its slope represents the rate of decomposition of the cellulose in the landfill 11 as a function of time. In addition, the curve 28 can be extrapolated as shown by the dashed line segments 29 and 31 to provide information as to the original cellulose content of the landfill and as to estimated future and past rates of decomposition. In addition, the original cellulose content can also be obtained from analysis of the incoming refuse or be estimated from typical refuse analysis which is reasonably consistent on a nationwide average.

In order to determine the methane potential, the amount of undecomposed cellulose remaining in the landfill should be ascertained. To determine the amount of cellulose in each zone, the percent cellulose for that zone, as determined by the sampling and measuring techniques disclosed above, is multiplied times the approximate total weight of the material in that zone.

To determine the relevant percent cellulose to utilize, it is first necessary to identify the period of time for which the methane potential is to be ascertained. If the total methane potential based upon the total cellulose remaining in the landfill is to be determined, the percent cellulose for each of the zones A-E can be read directly off the ordinate in FIG. 3. Alternatively, if the methane potential for some shorter time period is to be ascertained, it is necessary to substract from the total cellulose percentage the percent of undecomposed cellulose remaining after such time period. For example, if the methane production of the landfill for the five years immediately following the sampling date is to be determined, the percent of cellulose remaining in the zone A five years after the sampling date is determined by moving to the right along the abscissa in FIG. 3 from the zone A a distance corresponding to five years to locate a point on the curve 28 which is five years from the zone A. The percent cellulose for this point on the curve 28 is then determined and subtracted from the total cellulose in the zone A as of the sampling date to provide the percent of cellulose that will decompose in the zone A within the first five years after the sampling date. This procedure can then be repeated for the zones B-E to ascertain the amount of cellulose in each of these zones that can be expected to decompose within the five years following the sampling date. Of course, the amount of cellulose which can be expected to decompose during any other time period can be determined in the same manner.

The weight of the material in each zone as of the sampling date can be approximated using various different methods. For example, bores may be drilled in each of the zones, and the refuse taken from the bores and the bore volumes can be measured to determine the approximate density for each zone. Alternatively, empirical landfill densities can be used.

The volume of each zone is then determined by measuring the relevant dimensions of each zone. The density figure is then multiplied by the approximate volume of each zone to provide the total weight of each zone as of the sampling date.

By multiplying the relevant percent cellulose in each zone by the weight of material in that same zone, the total cellulose remaining for decomposition in all zones during the selected time span can be calculated. The methane which will be produced by this weight of cellulose can be determined using a stoichiometric equation. Although this is a two-step reaction, the overall stoiciometry is illustrated by way of example as follows:

$$(C_6H_{10}O_5)_x + H_2O \rightarrow 3CH_4 + 3CO_2$$

Utilizing the technique illustrated in FIG. 3, the sampling error is relatively large as shown by the length of each of the bars A'-E'. To reduce sampling error, and to help assure that unusual compositions in a given sample do not result in wild variations in the results, the percent cellulose to percent lignin ratio can be used.

Lignin is relatively nondecomposable, and ordinarily there is a strong positive correlation between the quantity of cellulose and the quantity of lignin in the refuse at the time the refuse is placed in the landfill. Also, cellulose and lignin are normally found together in refuse in relatively predictable ratios to each other at the time the refuse is placed in the landfill. The cellulose-to-lignin ratio may be determined by dividing the percent cellulose by weight by the percent lignin by weight with both of the percents being determined on a dry basis.

The cellulose-to-lignin ratio for each of the samples in each of the zones is plotted in FIG. 4 in the same manner as described above for the percent cellulose in FIG. 3. A curve 28a with extrapolated end portions 29a and 31a is then constructed in the same manner as the curve 28.

By using the cellulose-to-lignin ratio, the variation in the samples for each of the zones A-E is significantly reduced as shown by the relatively shorter bars A'-E' in FIG. 4. Accordingly, the curve 28a is more accurate than the curve 28 of FIG. 3. The curve 28a of FIG. 4, like the curve 28 of FIG. 3, gives a graphical presentation of the decomposition process in the landfill 11. This allows one to avoid sampling refuse typical of all of the many ages of the refuse in the landfill 11. It also permits comparisons to be made among landfills. The slope of the curve 28a of FIG. 4 is related to the rate of cellulose decomposition as a function of time.

Because the curve 28a can reasonably be expected to be more accurate than the curve 28, more accurate predictions as to methane potential can be obtained.

For example, if it is desired to find the total weight of cellulose in the landfill which is available for decomposition, the cellulose-to-lignin ratio for the zone A is multiplied by the number of tons of lignin in the zone A to provide the total weight of cellulose remaining in the zone A as of the sampling date.

The tons of lignin in the zone A can be estimated or determined in different ways. However, a preferred method is to measure the percent lignin for different zones in the landfill. This can be done using the landfill samples previously taken. The percent lignin is then multiplied by the total tons of refuse initially placed in the zone A to provide the total weight of lignin in the zone A. The landfill tonnage records can be used to ascertain the total weight of refuse in the zone A as of the time of placement. Because lignin is relatively non-decomposable in the landfill, the weight of lignin as of the date of placement is assumed to be the same as the weight of lignin as of the sampling date.

The result of the above calculations is the total weight of cellulose remaining in the zone A. The total weight of cellulose remaining in the zones B-E can be calculated in the same manner. The amount of methane which this weight of cellulose can be expected to produce can be calculated stoicometrically as described above with reference to FIG. 3.

If it is desired to calculate the methane potential of the landfill during a shorter time period, such as five years, the cellulose-to-lignin ratio for the zone A five years after the sampling date is determined from the curve 28a in FIG. 4. The cellulose remaining in the zone A at this five-year date is determined using the same procedure as described above, and once obtained, is substracted from the total amount of cellulose in the zone A as of the sampling date. This provides the weight of cellulose in the zone A that can be expected to decompose within the five-year period immediately following the sampling date. This procedure is then repeated for the zones B–E, and the results are summed to provide the total weight of cellulose in the landfill which can be expected to decompose within the five years following the sampling date. This weight of cellulose can be used as described above to determine the methane potential of the landfill during this five-year period.

In addition to the procedure described above, the percent of lignin can be estimated if the percent of inorganics in the originally placed refuse can be estimated. For example, if the refuse samples for the zone A show 20 percent lignin and 50 percent inorganic matter, and it can be estimated that the originally placed dry refuse had 30 percent inorganic matter, then the original refuse contained about 12 percent lignin. Specifically, the refuse existing at the time of the sample must have been derived from 50 divided by 0.3 or 167 pounds of refuse, of which 20 pounds was lignin, or about 12 percent lignin. In the calculations relating to FIG. 4, the percent lignin and the weight of refuse can be based on either wet or dry weight so long as they are consistent.

After the methane potential of the landfill has been determined, it must then be ascertained whether or not the methane potential is sufficient to warrant the installation of a landfill gas recovery plant or a recovery and purification plant. If the methane potential is sufficient and the landfill structure is appropriate for landfill gas extraction, a landfill recovery and purification plant of the type described in Bingham U.S. Pat. No. 4,000,990, or another suitable plant, may be installed.

In the specific examples given above, the selected fraction consists essentially of cellulose. If the selected fraction includes cellulose as a major component but does not consist essentially of cellulose, the steps of zone selection, sampling and measurement of the selected fraction content of each of the samples can be carried out as described above. The selected fraction content can then be plotted in FIG. 3 in lieu of percent cellulose and in lieu of the cellulose portion of the cellulose-to-lignin ratio in FIG. 4. The curves of FIGS. 3 and 4 would then represent the rate of decomposition within the landfill even if the selected fraction includes nondecomposables. Using these curves, the total decomposable content of the landfill can be determined to thereby permit calculation of the methane potential. An appropriate stoichiometric equation that represents the overall composition of whatever is being decomposed to produce methane can then be used to approximate the methane potential. In the time span under consideration for methane production in a landfill, such decomposable material is typically substantially entirely cellulose as most of the other decomposables of interest in a landfill decompose more rapidly than does cellulose.

Although an exemplary embodiment of the invention has been shown and described, many changes, modifications and substitutions may be made by one having ordinary skill in the art without necessarily departing from the spirit and scope of this invention.

I claim:

1. A method of testing a landfill for its methane potential comprising:
    selecting a landfill which contains a selected fraction with said selected fraction consisting essentially of cellulose;
    locating a plurality of zones within the landfill with each of said zones acting substantially uniformly with respect to decomposition of the selected fraction;
    taking at least one sample of the material of the landfill at each of said zones;
    measuring the selected fraction content of each of said samples; and
    utilizing the measured selected fraction content of at least some of said samples to find the approximate methane potential of the landfill.

2. A method as defined in claim 1 wherein said step of taking includes taking a plurality of samples of the material of the landfill in at least some of said zones.

3. A method as defined in claim 1 wherein said step of locating includes locating a plurality of zones within the landfill with at least a first group of said zones having been placed in the landfill at sufficiently different times so as to provide the selected fraction in each of said first group of zones with an opportunity to experience different amounts of decomposition following placement in the landfill.

4. A method as defined in claim 3 wherein said method includes the additional step of utilizing the measured selected fraction content to find the approximate rate of decomposition of the landfill.

5. A method as defined in claim 4 wherein said step of utilizing includes utilizing the measured selected fraction content to find the approximate methane potential of the landfill for N years where N is any number less than the time required for total decomposition of all of the cellulose remaining in the landfill.

6. A method of testing a landfill for its methane potential comprising:
    selecting a landfill which contains a significant first fraction and a significant nondecomposable fraction wherein the first fraction includes decomposable material the decomposition of which is related to methane production;
    locating a plurality of zones within the landfill with each of said zones having at least one different characteristic with respect to decomposition of said first fraction;
    taking at least one sample of the material of the landfill at each of said zones;
    measuring the content of each of said fractions in each of said samples; and
    utilizing the ratio of one of said fraction contents to the other of said fraction contents for at least some of said samples to find the approximate methane potential of the landfill.

7. A method as defined in claim 6 wherein said significant nondecomposable fraction consists essentially of lignin.

8. A method as defined in claim 6 wherein said step of selecting includes selecting a landfill wherein the quantity of said first fraction varies with the quantity of said nondecomposable fraction at the time of placement of refuse in the landfill.

9. A method as defined in claim 6 wherein said decomposable material includes cellulose and said nondecomposable fraction includes lignin.

10. A method as defined in claim 6 wherein said at least one different characteristic is time of placement in the landfill and said step of utilizing includes utilizing said ratios for said some of said samples to establish a relationship between said ratios and time of placement in the landfill and utilizing said relationship to find the approximate methane potential of the landfill.

11. A method as defined in claim 10 wherein said decomposable material includes cellulose and said non-decomposable fraction includes lignin, said step of taking includes taking a plurality of samples of the material of the landfill at each of said zones, and utilizing said relationship to find the approximate rate of decomposition of the decomposable material of the landfill.

* * * * *